(12) United States Patent
Boot et al.

(10) Patent No.: US 10,261,204 B2
(45) Date of Patent: Apr. 16, 2019

(54) METHODS AND SYSTEMS FOR SCAN ANALYSIS OF A CORE SAMPLE

(71) Applicant: GE Energy Oilfield Technology, Inc., Houston, TX (US)

(72) Inventors: John Christopher Boot, Atlanta, GA (US); Ali Can, Niskayuna, NY (US)

(73) Assignee: GE Energy Oilfield Technology, Inc., Houston, TX (US)

( * ) Notice: Subject to any disclaimer, the term of this patent is extended or adjusted under 35 U.S.C. 154(b) by 0 days.

(21) Appl. No.: 14/981,296

(22) Filed: Dec. 28, 2015

(65) Prior Publication Data

US 2016/0187509 A1 Jun. 30, 2016

Related U.S. Application Data

(60) Provisional application No. 62/098,775, filed on Dec. 31, 2014.

(51) Int. Cl.
| | | |
|---|---|---|
| *G01V 1/30* | (2006.01) | |
| *G06T 3/40* | (2006.01) | |
| *G06T 7/37* | (2017.01) | |

(52) U.S. Cl.
CPC .............. *G01V 1/30* (2013.01); *G06T 3/4038* (2013.01); *G06T 7/37* (2017.01); *G06T 2200/04* (2013.01)

(58) Field of Classification Search
None
See application file for complete search history.

(56) References Cited

U.S. PATENT DOCUMENTS

| | | | |
|---|---|---|---|
| 3,704,898 A | 12/1972 | Schmidt | |
| 3,746,369 A | 7/1973 | Neff | |
| 4,244,417 A | 1/1981 | Taylor | |
| 4,571,491 A | 2/1986 | Vinegar et al. | |
| 4,583,242 A * | 4/1986 | Vinegar ................. | G01N 33/24 378/20 |
| 4,616,134 A | 10/1986 | Pruett et al. | |

(Continued)

FOREIGN PATENT DOCUMENTS

GB 2135049 8/1984

OTHER PUBLICATIONS

Renard et al. "3D imaging of fracture propagation using synchrotron X-ray microtomography," Earth and Planetary Science Letters, 286, 2009, pp. 285-291.*

(Continued)

*Primary Examiner* — Soo Shin
(74) *Attorney, Agent, or Firm* — Hogan Lovells US LLP

(57) ABSTRACT

System for analyzing scan data of a core sample includes an imaging system for obtaining images of a first segment and a second segment of the core sample, and one or more processors for receiving the images of the first segment and the second segment, and setting the images of the first segment adjacent to the images of the second segment coaxially in series to form a stacked image. The method includes receiving image data of segments of the core sample, determining values representative of one or more physical characteristics of the core sample, comparing the values to known reference information of a material similar to the material of the core sample, and determining the one or more physical characteristics of the core sample based at least in part on the comparison.

20 Claims, 6 Drawing Sheets

(56) References Cited

U.S. PATENT DOCUMENTS

| | | | |
|---|---|---|---|
| 4,722,095 A * | 1/1988 | Muegge | G01N 15/088 250/252.1 |
| 4,909,557 A | 3/1990 | De Weck et al. | |
| 4,924,187 A * | 5/1990 | Sprunt | G01N 27/041 324/376 |
| 4,977,586 A | 12/1990 | Curry | |
| 5,025,150 A | 6/1991 | Oldham et al. | |
| 5,109,398 A * | 4/1992 | Hunt | G01N 15/082 250/253 |
| 5,153,899 A | 10/1992 | Curry | |
| 5,318,123 A * | 6/1994 | Venditto | E21B 43/26 166/250.1 |
| 5,360,066 A * | 11/1994 | Venditto | E21B 43/119 166/250.1 |
| 5,386,875 A | 2/1995 | Venditto et al. | |
| 5,409,251 A | 4/1995 | Thorndyke | |
| 5,509,687 A | 4/1996 | Thorndyke | |
| 5,671,136 A * | 9/1997 | Willhoit, Jr. | G01V 1/30 702/18 |
| 5,712,893 A | 1/1998 | Dykster et al. | |
| 5,947,213 A | 9/1999 | Angle et al. | |
| 6,118,839 A * | 9/2000 | Dafni | A61B 6/032 378/15 |
| 6,430,547 B1 | 8/2002 | Busche | |
| 6,481,887 B1 | 11/2002 | Mirabella | |
| 6,816,787 B2 | 11/2004 | Ramamoorthy | |
| 6,940,941 B2 | 9/2005 | Gregerson et al. | |
| 7,082,185 B2 | 7/2006 | Freifeld et al. | |
| 7,113,569 B2 | 9/2006 | Okumura et al. | |
| 7,172,038 B2 * | 2/2007 | Terry | G01V 3/30 175/320 |
| 7,175,347 B2 | 2/2007 | Tybinkowski et al. | |
| 7,500,388 B2 * | 3/2009 | Fujisawa | E21B 49/06 73/152.11 |
| 7,564,944 B2 | 7/2009 | Kato | |
| 7,714,304 B2 | 5/2010 | Poglitsch | |
| 7,853,045 B2 | 12/2010 | Touati | |
| 7,866,386 B2 | 1/2011 | Beer et al. | |
| 8,068,579 B1 | 11/2011 | Yun et al. | |
| 8,081,796 B2 | 12/2011 | Derzhi et al. | |
| 8,081,802 B2 | 12/2011 | Dvorkin et al. | |
| 8,085,974 B2 | 12/2011 | Dvorkin et al. | |
| 8,155,377 B2 | 4/2012 | Dvorkin et al. | |
| 8,170,799 B2 | 5/2012 | Dvorkin et al. | |
| 8,234,912 B2 | 8/2012 | Suarez-Rivera et al. | |
| 8,327,932 B2 | 12/2012 | Karanikas et al. | |
| 8,331,626 B2 | 12/2012 | Wojcik et al. | |
| 8,542,793 B1 | 9/2013 | Jin | |
| 8,562,078 B2 | 10/2013 | Burns et al. | |
| 8,590,382 B2 | 11/2013 | Zaleski, Jr. et al. | |
| 8,636,323 B2 | 1/2014 | Prince-Wright et al. | |
| 8,657,000 B2 | 2/2014 | Willingham et al. | |
| 8,725,477 B2 * | 5/2014 | Zhang | E21B 49/00 703/10 |
| 9,063,247 B2 | 6/2015 | Li et al. | |
| 9,103,176 B2 | 8/2015 | Delmar et al. | |
| 9,196,058 B2 | 11/2015 | Mezghani | |
| 9,507,047 B1 | 11/2016 | Dvorkin et al. | |
| 9,573,434 B2 | 2/2017 | Boot et al. | |
| 2002/0018542 A1 | 2/2002 | Fenkart et al. | |
| 2003/0107735 A1 | 6/2003 | Bland et al. | |
| 2004/0218716 A1 | 11/2004 | Freifeld et al. | |
| 2005/0127620 A1 | 6/2005 | Amundson | |
| 2007/0061079 A1 * | 3/2007 | Hu | E21B 25/00 702/6 |
| 2008/0217559 A1 | 9/2008 | Poglitsch et al. | |
| 2009/0078467 A1 | 3/2009 | Castillo | |
| 2010/0250139 A1 | 9/2010 | Hobbs et al. | |
| 2011/0150177 A1 | 6/2011 | Groot | |
| 2011/0181701 A1 * | 7/2011 | Varslot | G06T 7/0026 348/46 |
| 2012/0029828 A1 * | 2/2012 | Pepper | G01V 1/301 702/16 |
| 2012/0136196 A1 | 5/2012 | Foxall et al. | |
| 2012/0148398 A1 | 6/2012 | Campbell et al. | |
| 2012/0230151 A1 * | 9/2012 | Almaguer | E21B 7/061 367/86 |
| 2013/0083888 A1 | 4/2013 | Jin | |
| 2013/0182819 A1 | 7/2013 | Dvorkin et al. | |
| 2013/0301794 A1 | 11/2013 | Grader et al. | |
| 2014/0086381 A1 * | 3/2014 | Grader | G06T 7/0004 378/4 |
| 2014/0119501 A1 | 5/2014 | O'Hare et al. | |
| 2014/0297584 A1 * | 10/2014 | Jenkins | G06F 17/30563 707/602 |
| 2014/0367086 A1 | 12/2014 | Arian et al. | |
| 2015/0044004 A1 | 2/2015 | Pham et al. | |
| 2015/0177409 A1 * | 6/2015 | Sofiienko | G01V 5/125 250/269.1 |
| 2015/0185122 A1 * | 7/2015 | Lakshtanov | G01N 1/286 378/4 |
| 2016/0131793 A1 * | 5/2016 | Szudajski | G01N 21/65 378/53 |
| 2017/0032532 A1 * | 2/2017 | Andersen | E21B 49/02 |
| 2017/0108483 A1 * | 4/2017 | Clark | G01N 33/24 |

OTHER PUBLICATIONS

Coles et al., "Use of Attenuation Standards for CAT scanning Applications Within Oil and Gas Production Research," 1992 SCA Conference Paper No. 9223.*

Renard et al. "3D imaging of fracture propagation using synchrotron X-ray microtomography," Earth and Planetary Science Letters, 286, 2009, pp. 285-291 (Year: 2009).*

Coles et al., "Use of Attenuation Standards for CAT scanning Applications Within Oil and Gas Production Research," 1992 SCA Conference Paper No. 9223 (Year: 1992).*

Reddy, B., et al., "An FFT-Based Technique for Translation, Rotation, and Scale-Invariant Image Registration" IEEE Transactions on Image Processing, vol. 5 No. 8, Aug. 1996; pp. 1266-1271.

Wang, Qiang, et al., "Automatic Registration of Remote Sensing Image with Moderate Resolution" College of Geoscience and Surveying Engineering, CUMT, Beijing, China; Apr. 24-26, 2012; pp. 404-409.

* cited by examiner

| Mineral | Range (%) | Density (g/cc) |
|---|---|---|
| Smectite | 0-32 | 2.35 |
| Chlorite | 0-10 | 2.55 |
| Potassium-Feldspar | 0-7 | 2.56 |
| Kaolinite | 0-13 | 2.60 |
| Albite | 0-7 | 2.62 |
| Quartz | 0-52 | 2.62 |
| Plagioclase | 0-13 | 2.68 |
| Illite | 0-46 | 2.70 |
| Calcite | 0-81 | 2.71 |
| Dolomite | 0-8 | 2.84 |
| Anhydrite | 0-2 | 2.97 |
| Apatite | 0-5 | 3.19 |
| Siderite | 0-13 | 3.96 |
| Pyrite | 0-11 | 5.01 |

FIG. 9

METHODS AND SYSTEMS FOR SCAN ANALYSIS OF A CORE SAMPLE

CROSS-REFERENCE TO RELATED APPLICATIONS

This Application claims the benefit of U.S. Provisional Application 62/098,775 filed on Dec. 31, 2014, the entire contents of which is incorporated herein by reference.

BACKGROUND

Technical Field

The present disclosure relates in general to methods and systems for analyzing a core sample from a wellbore. More specifically, the present disclosure relates to methods and systems for analyzing a core sample from scans of segments of the core sample.

Description of Related Art

Various techniques are currently in use for identifying the presence of hydrocarbons in subterranean formations. If there is none or limited number of production wells from a site or formation, candidate hydrocarbon sites can be determined via seismic exploration that involves imaging subsurface impedance variations using sound waves. Then exploration wells are typically drilled to take high resolution sensor measurements using downhole logging devices that interrogate the formation from within the wellbore. Example downhole exploration devices include ultrasonic tools that can transmit and receive sound signals, or ones that simply receive a sound signal generated at surface. Other devices collect and sample fluid from within the formation, or from within the wellbore. Active nuclear tools are also employed that direct radiation into the formation, and receive radiation that scatters from the formation, or passive nuclear devices such as gamma sensor that collects the natural radioactive radiation in the rock particularly in shales. Other tools such as resistivity and induction logs can provide information about fluids residing in the formation adjacent the wellbore, the type of fluid, and information about other materials next to the wellbore.

Logging downhole also is sometimes done while the wellbore itself is being drilled. The logging devices are usually either integral with a drill bit used during drilling, or on a drill string that rotates the drill bit. The logging devices typically are either nuclear, ultrasonic, resistivity or impedance based, and can be in some instances optical devices.

SUMMARY

In some instances, a core is taken from the wellbore and analyzed after being retrieved to the surface. Analyzing the core generally provides information about the porosity and/or permeability of the rock formation adjacent the wellbore. Cores are generally elongated cylindrical members and obtained with a coring tool having an open barrel for receiving and retaining the core sample. The core sometimes has a length ranging from 30 to 60 feet.

One example embodiment is a system for analyzing a core sample of a formation. The system includes an imaging system for obtaining one or more images of a first segment and a second segment of the core sample, the core sample having an axis; and one or more processors for receiving the one or more images of the first segment and the second segment, and setting the one or more images of the first segment adjacent to the one or more images of the second segment coaxially in series to form a stacked image.

Another example embodiment is a method for analyzing a core sample of a formation. The method includes receiving, by one or more processors, image data of one or more segments of the core sample, determining, by the one or more processors, one or more values representative of one or more physical characteristics of the core sample, comparing, by the one or more processors, the one or more values to known reference information of a material similar to the material of the core sample, and determining, by the one or more processors, the one or more physical characteristics of the core sample based at least in part on the comparison.

Another example embodiment is a non-transitory computer-readable medium having computer executable instructions that when executed cause a computer to perform the operations of receiving a first image of a first segment and a second image of a second segment of a core sample of a formation, and aligning the first image with the second image so that the adjacent images are in an azimuthal orientation with respect to one another, and the azimuthal orientation matches or correlates to an azimuthal orientation of adjacent segments that are represented by the respective images.

BRIEF DESCRIPTION OF DRAWINGS

Some of the features and benefits of the present invention having been stated, others will become apparent as the description proceeds when taken in conjunction with the accompanying drawings, in which:

FIG. 9 is a chart showing example density ranges for a plurality of minerals in a core sample.

Figure 2B:
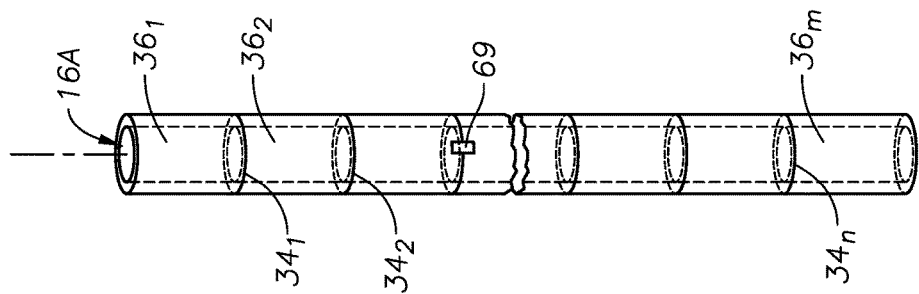
FIG. 2B is a perspective view of the core sample and sleeve of FIG. 2A cut into segments, according to one or more example embodiments.

While the invention will be described in connection with the preferred embodiments, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

Figure 1:
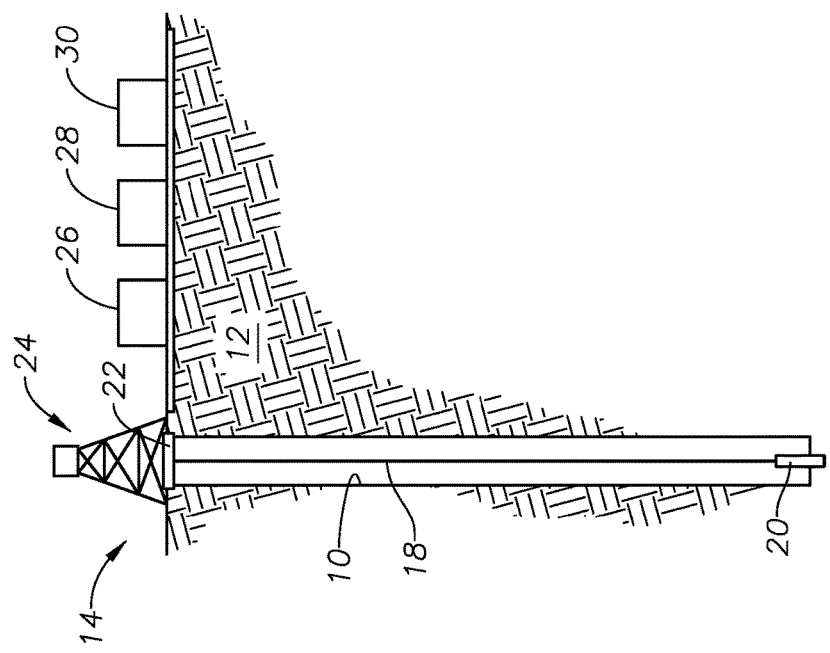
FIG. 1 is an elevational partial sectional view of an example of a system for obtaining a core sample, according to one or more example embodiments.

Shown in partial side sectional view in FIG. 1 is a wellbore 10 formed into a formation 12, a coring system 14 is deployed into the wellbore 10 for obtaining a core sample 16 (FIG. 2A) from within the wellbore 10. The coring system 14 includes a drill string 18 shown inserted into the wellbore 10, and with a coring bit 20 on its lower end that penetrates the formation 12 to retrieve the core sample 16. A drive table 22 is shown at the opening of the wellbore 10 for rotating the drill string 18 and bit 20. Alternative drive means for rotating the drill string 18 include a top drive (not shown) which could be mounted in a derrick 24 illustrated erected at an opening of the wellbore 10. Optionally, enclosures 26, 28, 30 are disposed adjacent the wellbore 10 and in which systems (FIG. 10) for analyzing the core sample 16 (FIG. 2A) are housed. Alternatively, analysis of the core sample 16 can take place remote from the wellbore 10.

Figure 2A:
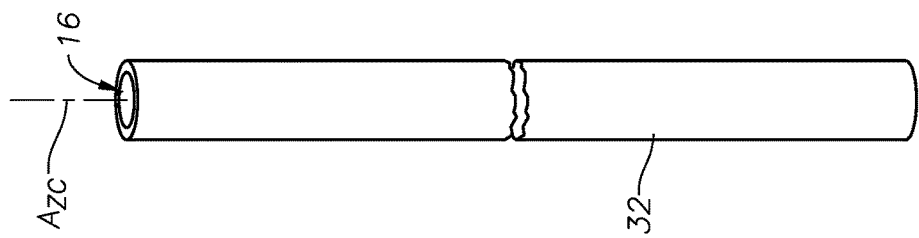
FIG. 2A is a perspective view of a core sample obtained with the system of FIG. 1 and inserted into a sleeve, according to one or more example embodiments.

FIG. 2A shows in a side perspective view the core sample 16 in a sleeve 32, where the annular sleeve 32 circumscribes the generally cylindrical core sample 16. In the illustrated example, core sample 16 and sleeve 32 are coaxially disposed about axis $A_{ZC}$. As shown in FIG. 2B, cuts $34_{1-n}$ are made along the core sample 16 and sleeve 32 to form a series of segments $36_{1-m}$ so that analysis of the rock making up the core sample 16 is more manageable. Embodiments exist where the segments $36_{1-m}$ have lengths that are about three feet or more.

Figure 3:
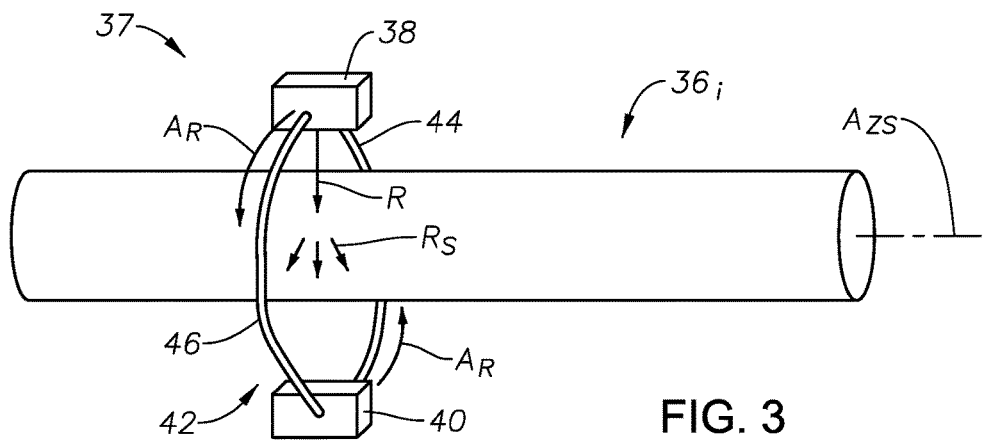
FIG. 3 is a perspective view of a one of the segments of FIG. 2B being imaged using a system, according to one or more example embodiments.

Schematically depicted in FIG. 3, is a perspective view of an example of an imaging system 37 for obtaining images of segments $36_i$ of the core sample 16 (FIG. 2B). Imaging system 37 includes a scan source 38, which in one embodiment includes a device for emitting radiation, such as but not limited to an X-ray. A scan receiver 40 is shown combined with scan source 38, which in one example, forms a scanner X-ray detector. Scan receiver 40 and scan source 38 are mounted on a gantry system 42 that is made up of curved supports 44, 46. Gantry system 42 provides a mounting assembly for scan source 38 and scan receiver 40; and which also rotates the scan source 38 and scan receiver 40 at an orbiting rotation around the segment $36_i$ and provides the scanning capabilities of the imaging system 37. Curved arrows $A_R$ provide one example direction of rotation of the gantry system 42 for orbiting the scan source 38 and scan receiver 40 around the segment $36_i$. Further in this example, during the step of imaging a manipulator system (not shown) may selectively move the segment $36_i$ bi-directionally along axis $A_{ZS}$. As the gantry system 42 orbits the scan source 38 and scan receiver 40 around the axially moving segment $36_i$, radiation R is emitted from the scan source 38 into the segment $36_i$. Some of the radiation R may be absorbed, scattered, or transmitted by the segment $36_i$, and amounts of each may be determined from the radiation received by the scan receiver 40. Additional characteristics of the radiation may be determined by the scan receiver 40. Non-limiting examples include changes in polarization, frequency, or type.

Figure 4:
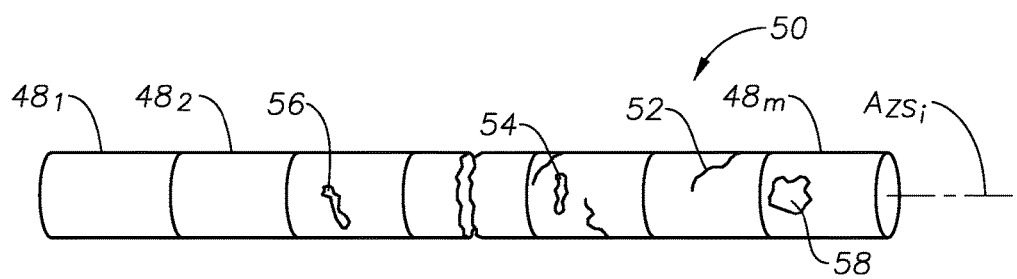
FIG. 4 is a perspective view of images of the segments of FIG. 2B arranged into a stacked image using a system, according to one or more example embodiments.

The scan receiver 40 collects the radiation R and scattered radiation $R_S$ at multiple angular locations about axis $A_{ZS}$ of the segment $36_i$. In the example illustrated in FIG. 4, the data collected by the scan receiver 40 is used, by one or more computer processors, to create segment images $48_{1-m}$, that each represent a one of the segments $36_{1-m}$, of FIG. 2B. As shown in FIG. 4, a visual representation of the segment images $48_{1-m}$ are set adjacent one another coaxially in series to define a stacked image 50. In an alternative, visually depicted in stacked image 50 are physical characteristics of the core sample 16 that were detected during the step of imaging described above. Example characteristics of the core sample 16 include hardness of the rock, fractures 52, voids 54, deposits 56, density, porosity, permeability, formation structure, bedding information, hydro-carbon content, water saturation, presence of non-rock matter, and other information reflective of the core sample 16. In one example embodiment, a value, set of values, or an index representative of one or more physical characteristics of the core sample 16 can be derived based on an analysis of the imaged data, which may or may not include reference to extrinsic data sources.

In an alternate embodiment, patterns 58 can be visually included with the stacked image 50. An example pattern 58 represents the presence of certain compounds (e.g. hydrocarbons) or types of matter (e.g. liquid, gas, solid) at a location in the core sample 16 that correlates to the location where the pattern 58 is disposed. A pattern 58 may also optionally represent a location in the core sample 16 where a substance or compound has a designated concentration. The information represented by the pattern 58 can be obtained using scanners, such as X-ray scanners, Raman spectrometers, near infrared spectrometers, laser induced ablation spectrometers, combinations thereof, and the like. For example, the scan source may include ionizing radiation or non-ionizing radiation. In an example, the stacked image 50 is made up of voxels, where each voxel represents a volume of the core sample 16, and where each voxel has a characteristic or value that relates back to the volume of the core sample 16 it represents. Embodiments exist where the characteristic or value of the voxel represents a physical characteristic of the volume of the core sample 16 relating to the voxel.

Figure 5:
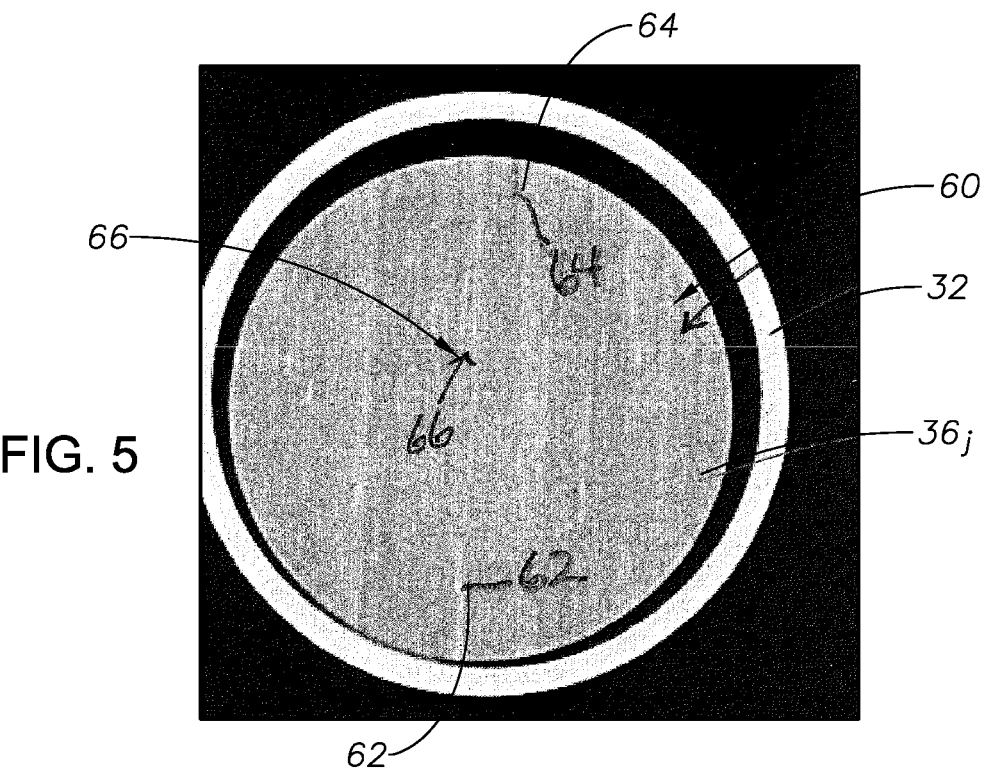
FIGS. 5 and 6 are end views of example segments of FIG. 2B, according to one or more example embodiments.
Figure 6:
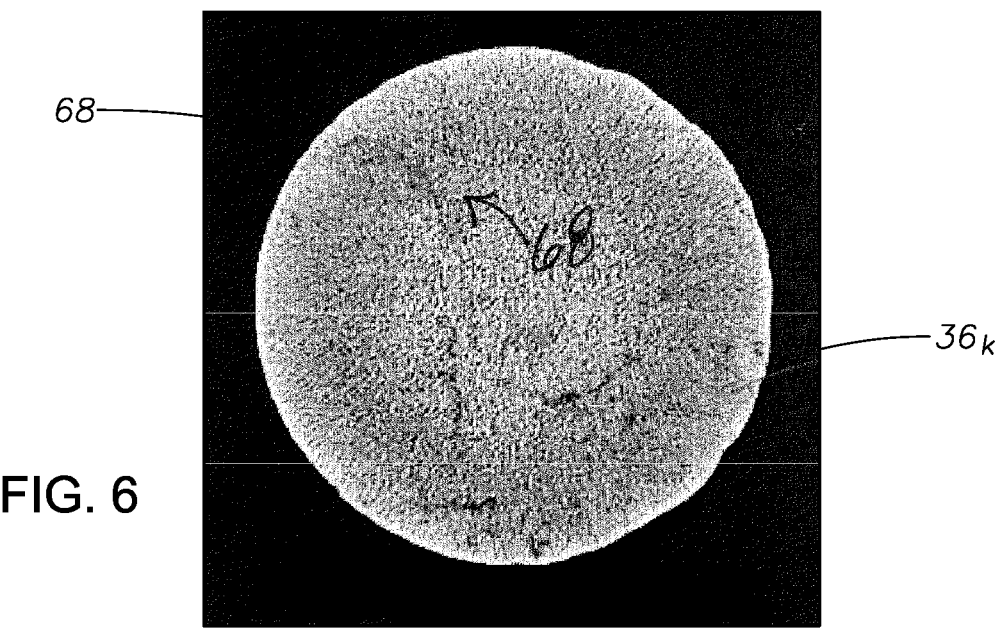

Axial end surfaces of example segments $36_j$, $36_k$ are shown in plan view respectively in FIGS. 5 and 6. In one example, segments $36_j$, $36_k$ are taken from a single core sample 16, segments $36_j$, $36_k$ can be adjacent to, or distal from, one another. The end surface of segment $36_j$ includes visually discernable variations. In the illustrated example, variations are manifested as striations 60 that extend radially and are generally parallel with one another. Within the striations 60 are lighter portions 62, darker portions 64, and spots 66. The end surface of $36_k$ is not striated, but instead has homogeneous sections and with elongated darker regions 68 randomly disposed thereon. Striations 60, lighter portions 62, darker portions 64, spots 66, and darker regions 68 can be used as markers to azimuthally register or index segments $36_j$, $36_k$, when the end surfaces of segments $36_j$, $36_k$ face the same cut 34 (FIG. 2B). Optionally, identifiable material 69 can be added to the core sample 16 and/or sleeve 32 (FIG. 2B) prior to forming the cuts $34_{1-n}$. The identifiable material 69 can be anything identifiable during the step of imaging, and examples include tape, paint, metal pins, coatings, adhesives, etc. In an example, corresponding segment images $48_j$, $48_k$ can visually represent the variations throughout the segments $36_j$, $36_k$ and on the end surfaces as described above.

In one embodiment, inherent variations or patterns in the images $48_j$, $48_k$ can define markers. Using the visual markers described above, an operator or an automated software system can with relative ease align segment images $48_i$, $48_{i+1}$, so that the adjacent segment images $48_i$, $48_{i+1}$ are in an azimuthal orientation with respect to one another that matches or correlates to an azimuthal orientation of adjacent segments $36_i$, $36_{i+1}$ that are represented by segment images $48_i$, $48_{i+1}$. Additionally, alignment of segment images $48_i$, $48_{i+1}$ may be achieved despite absence of some portion of the CT scan data or image as a result of material missing from core sample 16, e.g., as a result of the width of the cutting mechanism used to make cuts $34_{1-n}$. CT scan, also called X-ray computed tomography (X-ray CT) or computerized axial tomography scan (CAT scan), makes use of computer-processed combinations of many X-ray images taken from different angles to produce cross-sectional (tomographic) images (virtual 'slices') of specific areas of a scanned object, allowing the user to see inside the object without cutting. Embodiments include the use of an operator or a software system to align segment images $48_i$, $48_{i+1}$, so that the adjacent segment images $48_i$, $48_{i+1}$ are in an azimuthal orientation with respect to one another despite such gaps in scan or image data.

However, azimuthal alignment of the segment images $48_i$, $48_{i+1}$ is significantly more complicated when segment images $48_i$, $48_{i+1}$ are in digital form. One example method for azimuthal alignment of adjacent segment images $48_i$, $48_{i+1}$ includes a Fast Fourier Transform, as described in B. Reddy and B. Chatterji, "An FFT-Based Technique for Translation, Rotation, and Scale-Invariant Image Registration", *IEEE Trans. Image Processing*, vol., 5, No. 8, pp. 1266-1271, 1996, which is incorporated by reference herein in its entirety and for all purposes.

Another example method for azimuthal alignment of adjacent segment images $48_i$, $48_{i+1}$ includes automatic registration, as described in Q. Wang, Y Qiu, X Cui, G Wang, "Improved Automatic Registration Methods of Remote Sensing Image with Moderate Resolution", IJIIP, vol. 3, no. 3, pp 48-56, 2012, which is incorporated by reference herein in its entirety and for all purposes.

Figure 7:
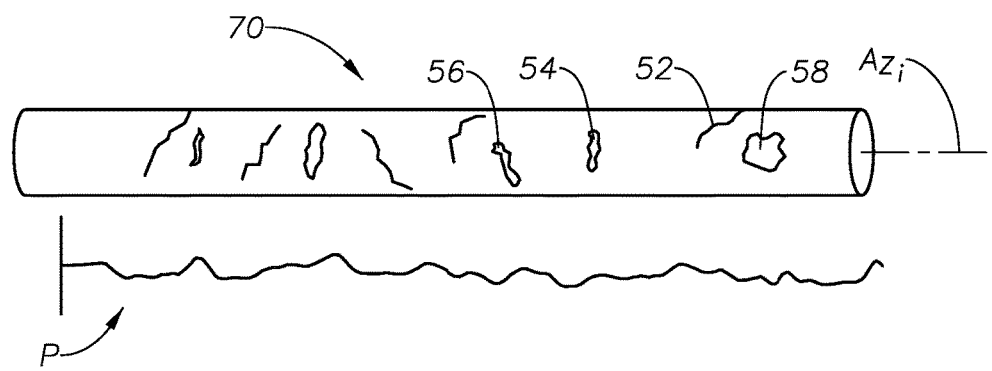
FIG. 7 is a perspective view of a consolidated image produced using a system, according to one or more example embodiments.

As shown in FIG. 7, by identifying markers in the adjacent images $48_j$, $48_k$, and azimuthally aligning the images $48_j$, $48_k$, an example of a composite image 70 can be created. In an embodiment, the composite image 70 visually represents core sample 16 (FIG. 2A). Moreover, further shown in composite image 70 are images of fractures 52, voids 54, deposits 56, and patterns 58 as depicted above and that correlate to the spatial location in the core sample 16 where these occlusions are disposed. Further provided in FIG. 7 is a plot P of an example of a logged record taken from the wellbore 10 (FIG. 1) that corresponds to the depths in the formation 12 from where the core sample 16 (FIG. 2A) was taken. As another example, plot P could be a graph of the average hardness, density, porosity, permeability, or other characteristic of core sample 16 at the corresponding location on composite image 70. Combining the values from the plot P with the information visually present on the composite image 70 provides further information for evaluating the formation 12. In an embodiment, characteristics of core sample 16 may be shown by values or symbols visually overlaid on top of segment image 48, or composite image 70 or portions thereof. These overlaid values or symbols may be in addition to or instead of a plot P adjacent to the image. Said overlaid values or symbols may indicate a measured or determined characteristic or value of core sample 16 at or near the corresponding overlaid location of segment image $48_i$ or composite image 70 or any portions thereof.

Further to cuts $34_{1-n}$, made in core sample 16, as previously described, there may be material missing, e.g., due to the width of a cutting mechanism such as a saw blade. In embodiments, composite image 70 therefore may visually incorporate one or more gaps (not shown) representative of the locations of missing material due to cuts $34_{1-n}$. It will be understood that other sources of missing material, divots, or voids, may be accommodated by the image alignment system and may be represented in segment image $48_i$ or composite image 70 or any portions thereof.

Advantages of viewing a composite image 70 instead of numerous segmented images, allows a greater amount of information to be analyzed simultaneously, so that a large-scale assessment of a larger volume of the formation 12 (FIG. 1) can be made. The attributes of the formation being assessed include its physical characteristics, such as fractures, voids, chemical compositions, and concentration of certain matter. Further embodiments of any particular segment image $48_i$ or composite image 70 include the ability to manipulate the zoom level of a view of segment image $48_i$ or composite image 70 when displayed on a display system. Embodiments of the invention include such a display system and appropriate user level inputs and display processing capability to enable zooming in and out. When zoomed in, a high level of detail may be available. When zoomed out, a lower level of detail may be displayed at a large scale, hence enabling identification of large scale features such as large fracture networks. Examples of level of detail include, but are not limited to, image detail, image resolution, number of characteristics or values overlaid with segment image $48_i$ or composite image 70 or portions thereof, and granularity of plot P. Accordingly, the cohesive approach of the present method makes possible a more accurate evaluation of formation permeability and other parameters that affect hydrocarbon production from the formation 12.

In embodiments, a subset of attributes, characteristics, or values determined from the scan data may be identified or selected to be stored as an index or key to the areas of core sample 16 or segment $36_i$. The indexes may be used to search for or locate specific areas of core sample 16 within the scan data or among or within segment images $48_{1-m}$ or composite image 70. As non-limiting examples, level of homogeneity or heterogeneity (high, medium, low) may be a searchable key characteristic. Additional non-limiting examples include existence, quantity, or sizes of ferrous material inclusions, pyrite inclusions, or fractures. The attributes or the quantization levels to be used as in index or key may be selected through processing by image or CT scan data processing systems. The selection may be automated and based upon the range of attributes, characteristics, or values present in the image data or scan data.

In a non-limiting example of a further embodiment, it may be desirable to determine, calculate, display, or otherwise represent the porosity or permeability of the material of core sample 16. Reference porosity information may be known of material similar to the material of core sample 16, for example from geologic reference tables or from prior analysis of a known reference core sample. If porosity or permeability information is known of the material making up a reference material, such as a reference core sample, by comparing the information known about the material of the reference with that obtained from the core sample 16, an estimate of the porosity or permeability of the core sample 16 can be derived. An advantage of this is especially evident when the imaging of the core sample 16 is performed proximate to the wellbore 10 and soon after being removed from the wellbore 10. In an embodiment, a reference core sample may be made up of a rock type similar to that of core sample 16, e.g., both core sample 16 and the reference core sample may be from a zone of tight sand stone.

If the same core is imaged at two different energies (dual energy), then from a set of dual energy images (e.g. low energy and high energy images) of a core, a Compton image and a Photoelectric image can be reconstructed using constraint non-linear optimization methods. Compton image and Photoelectric image represent the Compton coefficients and Photoelectric coefficients that are functions of physical properties of scanned materials, such as the mass, density, and effective atomic number. In one example embodiment, effective atomic number ($Z\_eff$) can be estimated from the Compton and Photoelectric images, and known Photoelectric and Compton coefficients of the core jacket material (such as aluminum) can be used to constrain the estimation of the $Z\_eff$ and material density.

In a non-limiting example of a further embodiment, using textural descriptors and dual energy signatures, lithology of the sample can be estimated via machine learning techniques. Using the dual energy measurements and known catalog of lithology material properties, the system may decompose the CT observations as a linear combination of basis material properties in the catalog. If the material property is mass attenuation coefficient of basis material, then linear attenuation coefficient may describe the mass density of the basis material. Hence percentage of porosity and hydrocarbon can be estimated if the lithology is correctly selected. For example in the presence of water filled porosity, negative logarithm of observed attenuation at a specific energy for a specific lithology may be defined as the linear sum of water density×water mass attenuation coefficient×f (porosity)+lithology density×lithology mass attenuation coefficient×f (1-porosity).

In this relationship, f (porosity) is a nonlinear function that relates the porosity to path length and density, and can be determined using calibration targets. Similar linear relationship can be used for hydrocarbon filled porosity.

In a particular non-limiting embodiment, the hardness index of core sample 16 may be determined from the CT scan data at various locations within core sample 16. The hardness index values may be compared to hardness index values from reference data to determine, calculate, or look up a porosity of core sample 16 in vicinity of the representative locations. For example, a reference core sample may have known or calculated porosity and known or calculated hardness index and serve as an indicator of the relation between such values in core sample 16.

Figure 8:
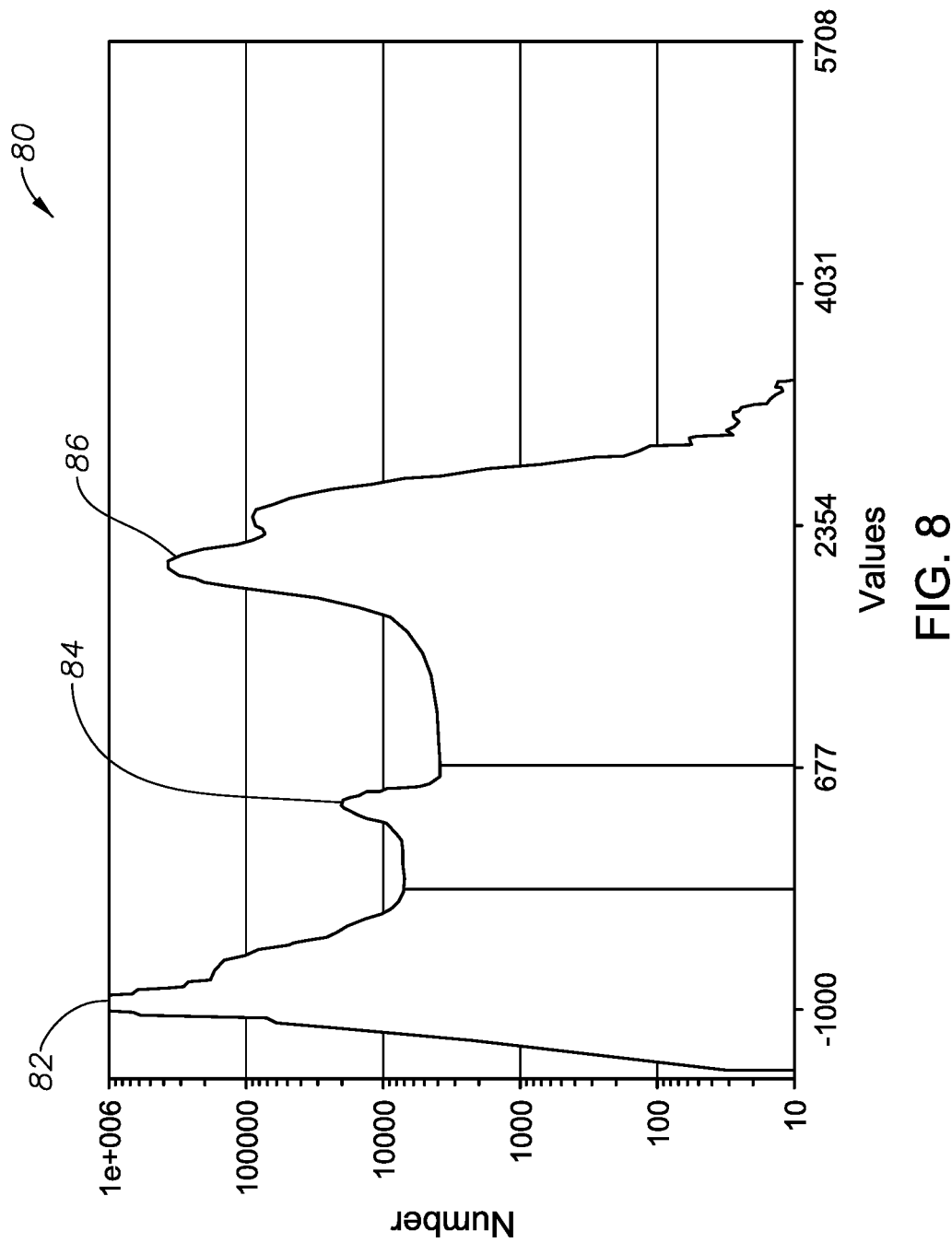
FIG. 8 shows an example method for analyzing scan data on a system, according to one or more example embodiments.

FIG. 8 illustrates an example method for analyzing scan data on a system, according to one or more example embodiments. In this non-limiting example, densities of pixels in an image of a segment of the core sample are plotted against the number of values obtained for every density. The resulting plot 80 shows a first peak 82, a second peak 84, and a third peak 86, which may indicate that there are at least three different minerals in the core sample. In a non-limiting example of a further embodiment, if densities of these minerals are compared to known reference values as shown in FIG. 9, for example, the system may also be able to determine the type of mineral present in the core sample.

Figure 10:
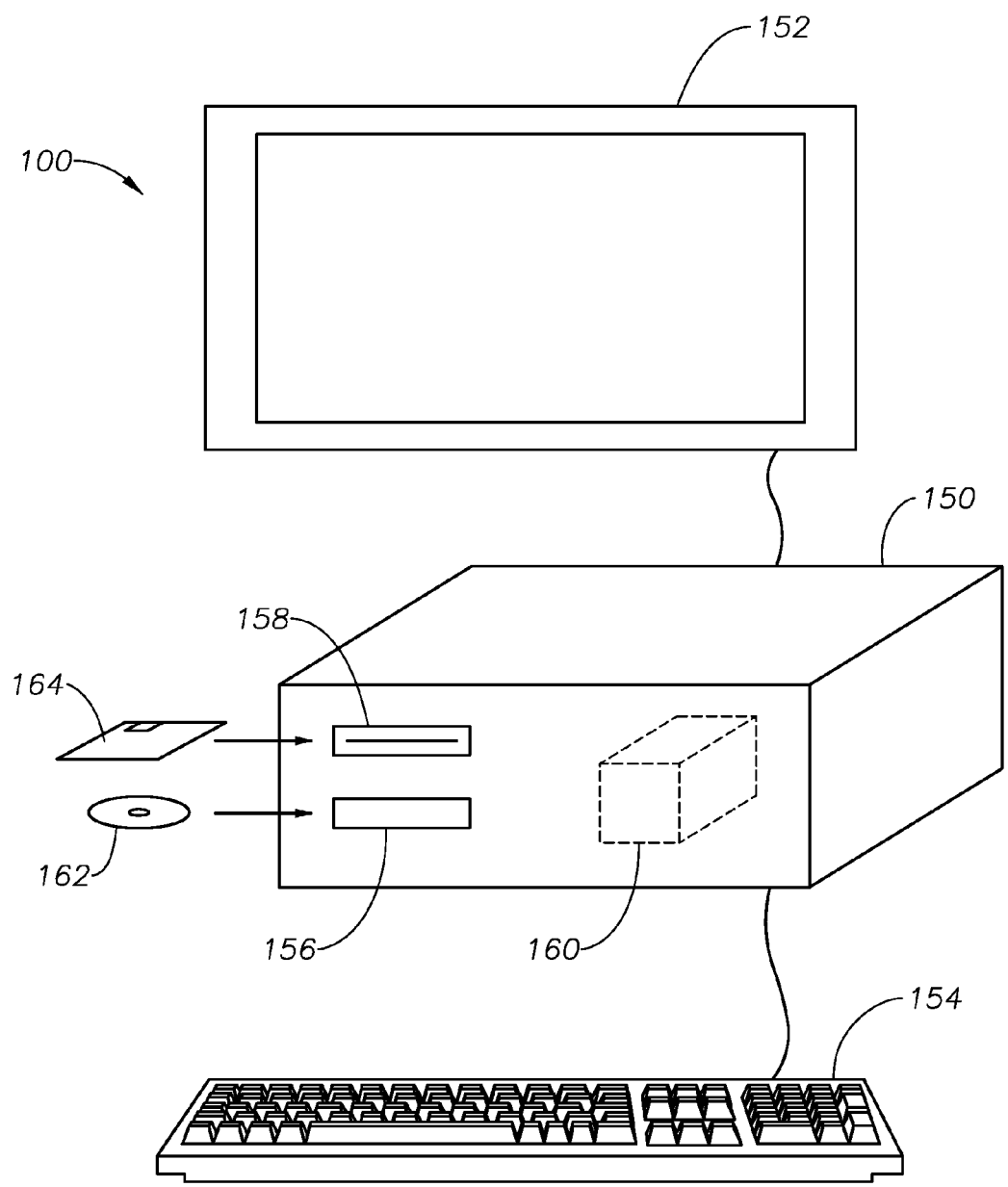
FIG. 10 illustrates an example system for scan analysis of a core sample, according to one or more example embodiments.

In another example embodiment, the invention relates to computer programs stored in computer readable media. Referring to FIG. 10, the foregoing process as explained with reference to FIGS. 3-9 can be embodied in computer-readable code. FIG. 10 illustrates an example system for scan analysis of a core sample, according to one or more example embodiments. The code can be stored on, e.g., a computer readable medium, such as a floppy disk 164, CD-ROM 162 or a magnetic (or other type) hard drive 160 forming part of a general purpose programmable computer 100.

The computer 100, as known in the art, includes a central processing unit 150, one or more disc drives 156, 158, a user input device such as a keyboard 154 and a user display 152 such as a flat panel LCD display. According to this aspect of the invention, the computer readable medium includes logic operable to cause the computer to execute acts as set forth above and explained with respect to the previous figures. For example, the central processing unit 150, which may include one or more processors, can perform the functions of scanning, storing, and analyzing images as illustrated in FIGS. 3-9.

The example computational environment shown in FIG. 10 is only illustrative and is not intended to suggest or otherwise convey any limitation as to the scope of use or functionality of such computational environments' architecture. In addition, the computational environment should not be interpreted as having any dependency or requirement relating to any one or combination of components illustrated in this example computational environment. The computational environment represents an example of a software implementation of the various aspects or features of the disclosure in which the processing or execution of operations described in connection with performing a maintenance action in accordance with this disclosure, can be performed in response to execution of one or more software components at the computing device. A software component can be embodied in or can comprise one or more computer-accessible instructions, e.g., computer-readable and/or computer-executable instructions. At least a portion of the computer-accessible instructions can embody one or more of the example techniques disclosed herein. For instance, to embody one such method, at least the portion of the computer-accessible instructions can be persisted (e.g., stored, made available, or stored and made available) in a computer storage non-transitory medium and executed by a processor. The one or more computer-accessible instructions that embody a software component can be assembled into one or more program modules, for example, that can be compiled, linked, and/or executed at the computing device or other computing devices. Generally, such program modules comprise computer code, routines, programs, objects, components, information structures (e.g., data structures and/or metadata structures), etc., that can perform particular tasks (e.g., one or more operations) in response to execution by one or more processors, which can be integrated into the computing device or functionally coupled thereto.

For purposes of simplicity of explanation, the example method disclosed herein is presented and described as a series of blocks (with each block representing an action or an operation in a method, for example). However, it is to be understood and appreciated that the disclosed method is not limited by the order of blocks and associated actions or operations, as some blocks may occur in different orders and/or concurrently with other blocks from those that are shown and described herein. For example, the various methods (or processes or techniques) in accordance with this disclosure can be alternatively represented as a series of interrelated states or events, such as in a state diagram. Furthermore, not all illustrated blocks, and associated action(s), may be required to implement a method in accordance with one or more aspects of the disclosure. Further yet, two or more of the disclosed methods or processes can be implemented in combination with each other, to accomplish one or more features or advantages described herein.

It should be appreciated that the techniques of the disclosure can be retained on an article of manufacture, or computer-readable medium, to permit or facilitate transporting and transferring such methods to a computing device (e.g., a desktop computer; a mobile computer, such as a tablet, or a smartphone; a gaming console, a mobile telephone; a blade computer; a programmable logic controller, and the like) for execution, and thus implementation, by a processor of the computing device or for storage in a memory thereof or functionally coupled thereto. In one aspect, one or more processors, such as processor(s) that implement (e.g., execute) one or more of the disclosed techniques, can be employed to execute code instructions retained in a memory, or any computer- or machine-readable medium, to implement the one or more methods. The code instructions can provide a computer-executable or machine-executable framework to implement the techniques described herein.

Unless otherwise expressly stated, it is in no way intended that any protocol, procedure, process, or method set forth herein be construed as requiring that its acts or steps be performed in a specific order. Accordingly, where a process or method claim does not actually recite an order to be followed by its acts or steps or it is not otherwise specifically recited in the claims or descriptions of the subject disclosure that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification or annexed drawings, or the like.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

The system and method described herein, therefore, are well adapted to carry out the objects and attain the ends and advantages mentioned, as well as others inherent therein. While example embodiments of the system and method have been given for purposes of disclosure, numerous changes exist in the details of procedures for accomplishing the desired results. In an example, the wellbore can be perforated, and the orientation of the perforations is based on information obtained from analyzing the composite image 70. These and other similar modifications may readily suggest themselves to those skilled in the art, and are intended to be encompassed within the spirit of the system and method disclosed herein and the scope of the appended claims.

What is claimed is:

1. A system for analyzing a core sample of a formation, the core sample having an axis, the system comprising:
   an imaging system having a scan source and a scan receiver, positioned adjacent the core sample with at least part of the core sample between the scan source and the scan receiver, wherein the imaging system obtains one or more images of a first segment and a second segment of the core sample as the core sample moves axially between the scan source and the scan receiver; and
   one or more processors for receiving the one or more images of the first segment and the second segment, setting the one or more images of the first segment adjacent to the one or more images of the second segment coaxially in series to form a three-dimensional stacked core image, and generating a plot that is aligned with a length of the three-dimensional stacked core image, the plot representing both a logged record and one or more characteristics of the core sample positioned at a corresponding location on the three-dimensional stacked core image.

2. The system of claim 1, wherein the scan source emits radiation.

3. The system of claim 2, wherein the radiation comprises ionizing radiation or non-ionizing radiation.

4. The system of claim 2, wherein the scan receiver receives at least a portion of the emitted radiation.

5. The system of claim 4, further comprising a mounting assembly for mounting the scan source and scan receiver, and adapted to rotate the scan source and scan receiver at an orbiting rotation around the first segment.

6. The system of claim 5, further comprising a manipulator system having a mounting assembly and curved supports, that selectively moves the first segment in one or more directions along an axis of the first segment.

7. The system of claim 1, wherein the stacked image comprises one or more characteristics of the core sample, wherein the one or more characteristics comprises at least one of hardness of the formation, fractures, voids, deposits, density, porosity, permeability, formation structure, bedding information, hydro-carbon content, water saturation, presence of non-rock matter, and other information reflective of the core sample.

8. A method for analyzing a core sample of a formation, the method comprising:
   generating image data of one or more segments of the core sample by transmission of radiation from a scan source, across the core sample, to a scan receiver;
   receiving, by one or more processors, image data of one or more segments of the core sample, the image data generated by
      transmitting radiation from a scan source across the first segment, to a scan receiver;
      changing the axial position of the core sample between the scan source and the scan receiver; and
      transmitting radiation from the scan source across the second segment, to the scan receiver;
   obtaining, by an imaging system, one or more images of a first segment and a second segment of the core sample;
   setting, by the one or more processors, the one or more images of the first segment adjacent to the one or more images of the second segment coaxially in series to form a three-dimensional stacked core image determining, by the one or more processors, one or more values representative of one or more physical characteristics of the core sample;

comparing, by the one or more processors, the one or more values to known reference information;

indexing the one or more values representative of one or more characteristics of the core sample, the index being searchable for specific areas of the core sample; and determining, by the one or more processors, the one or more physical characteristics of the core sample based at least in part on the comparison.

9. The method of claim 8, wherein the one or more physical characteristics comprises at least one of hardness of the formation, fractures, voids, deposits, density, porosity, permeability, formation structure, bedding information, hydro-carbon content, water saturation, presence of non-rock matter, and other information reflective of the core sample.

10. The method of claim 8, wherein the known reference information is obtained from geologic reference tables or from prior analysis of a known reference core sample.

11. The method of claim 8, further comprising: emitting radiation by a scan source for obtaining the one or more images of a first segment and a second segment of the core sample in the imaging system.

12. The method of claim 11, further comprising:
mounting the scan source and a scan receiver on a mounting assembly; and
rotating the scan source and scan receiver at an orbiting rotation around the first segment.

13. The method of claim 12, further comprising:
selectively moving the first segment in one or more directions along an axis of the first segment.

14. The method of claim 8, wherein the step of generating image data further comprises:
simultaneously rotating the scan source and scan receiver radially around the core sample while moving the core sample axially relative to the scan source and scan receiver to generate a helical scan.

15. A non-transitory computer-readable medium having computer executable instructions that when executed cause a computer to perform the operations of:
receiving a first image of a first segment and a second image of a second segment of a core sample of a formation, the first image and the second image generated by transmitting radiation from a scan source across the first segment, to a scan receiver;
changing the axial position of the core sample between the scan source and the scan receiver; and
transmitting radiation from the scan source across the second segment, to the scan receiver;

aligning the first image with the second image so that adjacent images are in an azimuthal orientation with respect to one another, the azimuthal orientation matches or correlates to the azimuthal orientation of adjacent segments that are represented by the respective images, and the adjacent images form a three-dimensional stacked core image; and generating a plot that is aligned with a length of the adjacent images in the azimuthal orientation, the plot representing one or more characteristics of the core sample positioned at a corresponding location along the azimuthal orientation and a logging record.

16. The non-transitory computer-readable medium of claim 15, wherein the computer executable instructions further cause the computer to perform the operations of:
determining one or more values representative of one or more physical characteristics of the core sample;
comparing the one or more values to known reference information; and
determining the one or more physical characteristics of the core sample based at least in part on the comparison.

17. The non-transitory computer-readable medium of claim 15, wherein the one or more physical characteristics comprises at least one of hardness of the formation, fractures, voids, deposits, density, porosity, permeability, formation structure, bedding information, hydro-carbon content, water saturation, presence of non-rock matter, and other information reflective of the core sample.

18. The non-transitory computer-readable medium of claim 15, wherein the known reference information is obtained from geologic reference tables or from prior analysis of a known reference core sample.

19. The non-transitory computer-readable medium of claim 15, wherein the computer executable instructions further cause the computer to perform the operations of:
setting the first image of the first segment adjacent to the second image of the second segment coaxially in series to form the three-dimensional stacked core image.

20. The non-transitory computer-readable medium of claim 15, wherein the first image or the second image comprises CT scan data.

* * * * *